(12) United States Patent  
Kreindel

(10) Patent No.: US 7,041,100 B2
(45) Date of Patent: May 9, 2006

(54) METHOD AND SYSTEM FOR SELECTIVE ELECTRO-THERMOLYSIS OF SKIN TARGETS

(75) Inventor: Michael Kreindel, Haifa (IL)

(73) Assignee: Syneron Medical Ltd., Yokneam Ellit (IL)

( * ) Notice: Subject to any disclaimer, the term of this patent is extended or adjusted under 35 U.S.C. 154(b) by 148 days.

(21) Appl. No.: 10/760,719

(22) Filed: Jan. 21, 2004

(65) Prior Publication Data

US 2005/0159737 A1    Jul. 21, 2005

(51) Int. Cl.
*A61B 18/18* (2006.01)

(52) U.S. Cl. .......................................... 606/41; 128/898
(58) Field of Classification Search ................ 128/898; 606/27–52
See application file for complete search history.

(56) References Cited

U.S. PATENT DOCUMENTS

| 5,122,137 | A |   | 6/1992 | Lennox |
| 5,217,455 | A | * | 6/1993 | Tan ................................ 606/9 |
| 5,755,753 | A |   | 5/1998 | Knowlton |
| 6,210,402 | B1 | * | 4/2001 | Olsen et al. .................. 606/32 |

* cited by examiner

*Primary Examiner*—Roy D. Gibson
*Assistant Examiner*—Pete Vrettakos
(74) *Attorney, Agent, or Firm*—Nath & Associates PLLC; Gary M. Nath; Viviana Amzel

(57) ABSTRACT

A method for non-invasive selective thermal destruction of a skin target by RF current. One or more characteristics of an RF current and a bipolar RF electrode system are determined based upon one or more features of the target in order to create in the target an average energy density exceeding 5 Joules/cm$^3$ but lower than a skin coagulation level. The determined electrode system is then applied to the skin and an average energy density exceeding 5 Joules/cm$^3$ but lower than a skin coagulation level is generated in the target.

11 Claims, 2 Drawing Sheets

METHOD AND SYSTEM FOR SELECTIVE ELECTRO-THERMOLYSIS OF SKIN TARGETS

FIELD OF THE INVENTION

The present invention is related to methods for treating skin.

BACKGROUND OF THE INVENTION

The term "skin target", is used to refer to an unwanted skin defect such as vascular and pigmented lesions, unwanted hairs, and acne. Selective thermolysis of a skin target refers to heating a skin target to a temperature sufficiently high to destroy the target (about 60–70° C.) without heating the surrounding healthy skin to a damaging level. In this method, the skin is irradiated with laser or incoherent light having a wavelength allowing it to penetrate into the tissue to the depth of the target. This method, however, works only when the target has a higher optical absorption coefficient that the surrounding tissue (i.e. the target is darker than the surrounding skin), otherwise it is not possible to sufficiently heat the target without heating the surrounding tissue to a damaging temperature. For example, a dark hair can be successfully destroyed in light skin. However, treatment of gray hairs is not effective due to a lack of melanin in the hair shaft to absorb the optical energy. Similarly, use of optical energy to destroy a skin target can only be applied with limited efficiency with dark skin. In order to reach the target such as a hair root or blood vessel, the light has to pass through the epidermis. A dark epidermis absorbs more light energy than a light epidermis. Thus, a higher light intensity must be used with dark skin, which increases the risk of burning the skin.

U.S. Pat. No. 5,755,753 describes a method for selective removal of hair using laser radiation, where the parameters of irradiation are optimized for selective light absorption by the melanin of the hair shaft.

An alternative method of tissue heating used in medicine is radio frequency (RF) energy. The electrical current generates an amount of heat in the tissue that depends on the current density and tissue conductivity. DC or AC electrical current causes muscle spasms and is dangerous for treatment, but high frequency RF current (>300 kHz) causes a pure thermal effect and can be used for skin treatment. The range of the frequencies higher than 20 MHz is difficult to implement. However, RF current is used only for non-selective treatment, i.e. it does not preferentially heat a skin target without overheating the surrounding skin. Therefore, the main applications of RF current are electro-surgery and blood coagulation. In both of these applications, the tissue is heated in an area adjacent to the applied electrodes to a coagulation or ablative level. For example, U.S. Pat. No. 5,122,137 describes a coagulator with controlled temperature. The U.S. Pat. No. 5,755,753 describes a device for non-selective heating of the dermis and epidermis with a unipolar RF system in combination with cooling of the epidermis. Using this method, it is possible to obtain a temperature of the dermis that is higher than the temperature of the epidermis. This method however does not provide selective heating of the target by the RF current and is therefore limited to only one application.

DESCRIPTION OF THE INVENTION

The present invention is based upon the novel and unexpected finding that a difference in the electrical properties of different skin parts can be utilized for selective treatment of a skin target by RF current. Thus, parameters of an RF current through skin tissue can be optimized for selective destructive heating of skin targets by the RF current without causing damage to the surrounding tissue. Thus, in its first aspect, the present invention provides a method for the selective thermolysis of skin targets by RF currents. In its second aspect, the invention provides a system for carrying out the method of the invention.

In accordance with the method of the invention, the value of one or more parameters of the RF energy to be applied to the skin is determined based upon one or more features of the target to be treated. The RF parameters that may be selected include, for example, the electric current, the geometry of the electrodes, the energy level and pulse duration.

Electrode Geometry

In one embodiment of the invention, a bipolar electrode system is used and the geometry of the electrodes is determined based upon one or more features of the target to be treated. Unlike a unipolar electrode system, a bipolar system localizes the electrical current in the skin tissue between the two electrodes. The current penetration depth is approximately equal to half the distance between electrodes Thus, in accordance with this embodiment of the invention; the distance between the electrodes is selected that is about twice the target depth.

Also in accordance with this embodiment, the area of contact of the electrodes is selected based upon the features of the skin target to be treated. Electrical current density increases as the curvature of electrode increases. In order to avoid hot spots at the electrode edges, the contact area of the electrodes should be round (i.e. without any sharp corners). In order to avoid divergence of the electrical current in the skin between the electrodes, and the concentration of current on the contact surface of the electrodes, the applied surface area of the electrodes is selected to be approximately the same as the area of the skin where the RF current is to be applied. Hot spots may also be avoided by cooling the contact area of the electrodes.

Applied Energy

In accordance with another embodiment of the invention, the intensity of the electric energy generated by the RF current is selected based upon one or more features of the skin target to be treated.

The heating of a tissue by an RF current can be calculated using the Joule equation:

$$H = \sigma E^2 = \frac{j^2}{\sigma},$$

where E is the electric field strength and a is the conductivity of the tissue. Thus, a target with a higher conductivity than the surrounding tissue is heated by an electrical current more than the surrounding tissue. The conductivity of various biological tissues is presented in Table 1. Blood has the highest conductivity of all of the tissues in the Table. Thus, a skin target having a conductivity greater than the conductivity of the surrounding tissue may be selectively destroyed.

TABLE 1

Conductivity of different types of biological tissue at 1 MHz from S. Gabriel, et al., "The dielectric properties of biological tissues: III. Parametric models for dielectric spectrum of tissues". Phys. Med. Biol. 41: 2271–2293, 1996

| Tissue | Conductivity, S m$^{-1}$ |
| --- | --- |
| Blood | 0.7 |
| Bone | 0.02 |
| Fat | 0.03 |
| Dry skin | 0.03 |
| Wet skin | 0.25 |

Duration of Current Pulse

In accordance with yet another embodiment of the invention, the pulse duration of the applied RF energy is selected based upon one or more features of the skin target to be treated. Electrical energy should be delivered to the target during a time shorter than its cooling time to avoid energy dissipation from the target to the surrounding tissue. The cooling time of the target depends on its size and geometry. The cooling time t of a cylindrical object, for example, may be estimated using the equation $t=d^2/(16A)$, where d is the target diameter and A is the skin diffusivity which is similar to the diffusivity of water (about $1.4 \times 10^{-3}$ cm$^2$/sec). Thus, in accordance with this embodiment of the invention, a pulse duration is selected to be approximately equal to the cooling time of the skin target to be treated.

The invention thus provides method for non-invasive selective thermal destruction of a skin target by RF current comprising:
  (a) determining one or more characteristics of an RF current and a bipolar RF electrodes system based upon one or more features of the target in order to create in the target an average energy density exceeding 5 Joules/cm$^3$ but lower than a skin coagulation level; and
  (b) applying to the skin the determined electrode system and generating in the target an average energy density exceeding 5 Joules/cm$^3$ but lower than a skin coagulation level.

BRIEF DESCRIPTION OF THE DRAWINGS

In order to understand the invention and to see how it may be carried out in practice, the invention will be described, by way of non-limiting example only, with reference to the accompanying drawings, in which.

DETAILED DESCRIPTION OF THE INVENTION

Figure 1:
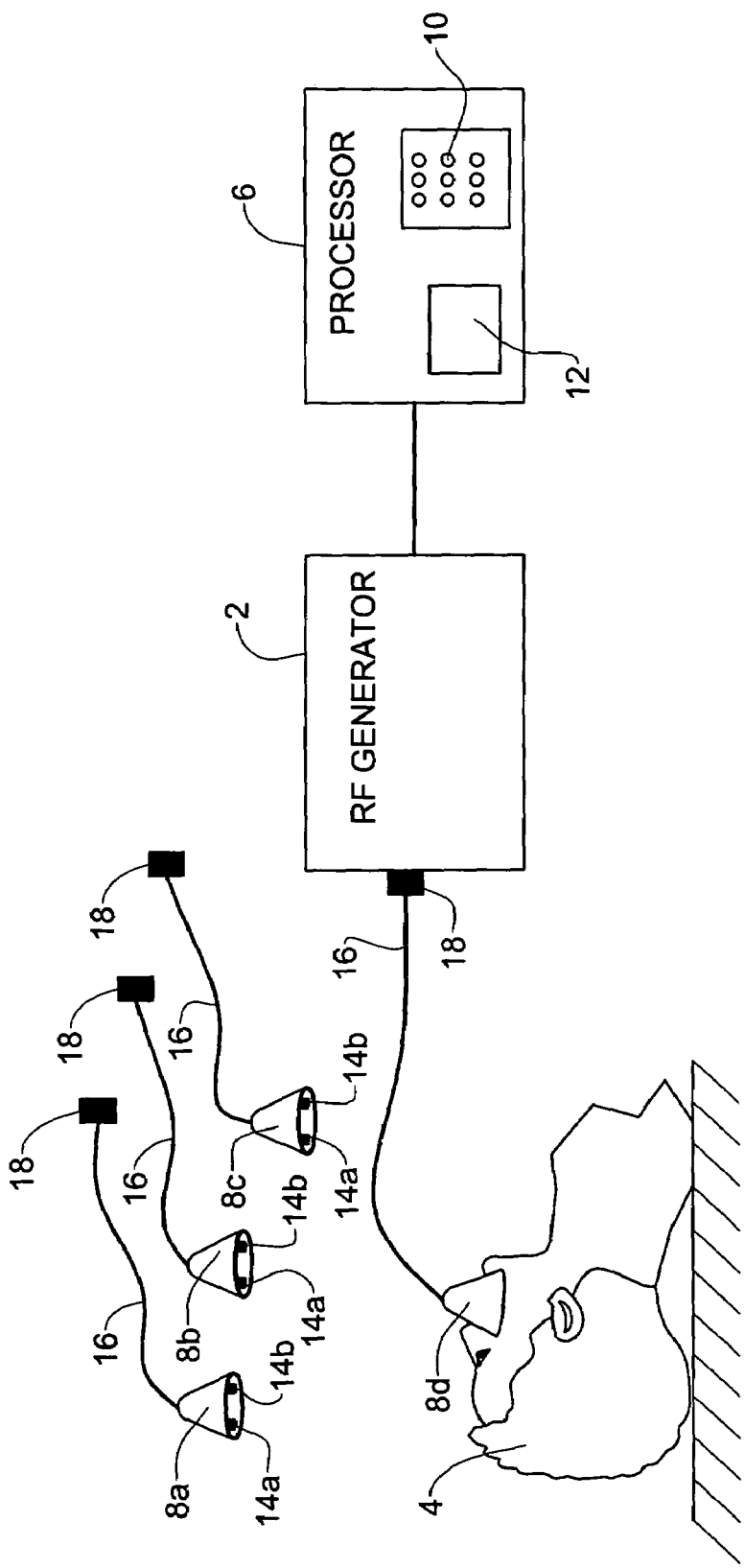
FIG. 1 shows a system for selective thermolysis using RF.

FIG. 1 shows a system 1 for selective thermolysis of a skin target with RF energy in accordance with one embodiment of the invention. The system 1 comprises an RF generator 2 that is used for applying an RF current to the skin of an individual 4. The system 1 further comprises a processor 6 that is configured to determine one or more parameters of an RF current to be applied to the individual 4 in order to destroy a skin target, based upon one or more features of the target. Associated with the processor 6 are one or more input devices such as a control panel 10 and a display 12. The system 1 further includes a plurality of RF applicators 8a to 8d. Each applicator 8 has a pair of electrodes 14a and 14b. The electrode pair 14a and b in each applicator 8 has different geometric characteristics (e.g. different contact areas and/or separation distances). Each applicator includes a cable 16 that terminates in a plug 18 for insertion into a mated socket on the RF generator 2, as shown for the applicator 8d.

In use, a caregiver is prompted by the processor 6 of the type of a skin target in the skin of the individual 4 to be destroyed. This may be done, for example, by the processor displaying on the display 12 a list of possible target types, and instructing the caregiver to select a target type from the list. The target type may be, for example, a hair, or a vascular lesion. The caregiver then selects the target type from the list using the control panel 10. The caregiver is then prompted by the processor 6 to input one or more features of the skin target to be destroyed. This may be done, for example, by the processor displaying on the display 12 a list of one or more features that apply to the target type that was previously selected. For example, if the target type is a vascular lesion, the processor would prompt the caregiver to input the diameter of the lesion and its depth.

Based upon the type and features of the target to be destroyed, the processor executes a program for determining the most appropriate applicator 10 to be used to destroy the target as well as one or more characteristics of the RF current that is to be used. The appropriate applicator and the current characteristics determined by the processor 6 are then displayed on the display 12. The caregiver may reject any one or more of the determinations made by the processor 6 using the control panel 10. The caregiver then connects the determined applicator 8 to the socket of the RF generator, as shown in FIG. 1 for the applicator 8d. The processor may be configured to set the RF generator 2 to generate an RF current having the determined characteristics. Alternatively, the caregiver may manually adjust the RF generator 2. The determined applicator is then applied to the skin of the individual 4 and the determined RF current is then applied to the skin.

EXAMPLES

Treatment of Blood Vessel

Figure 2:
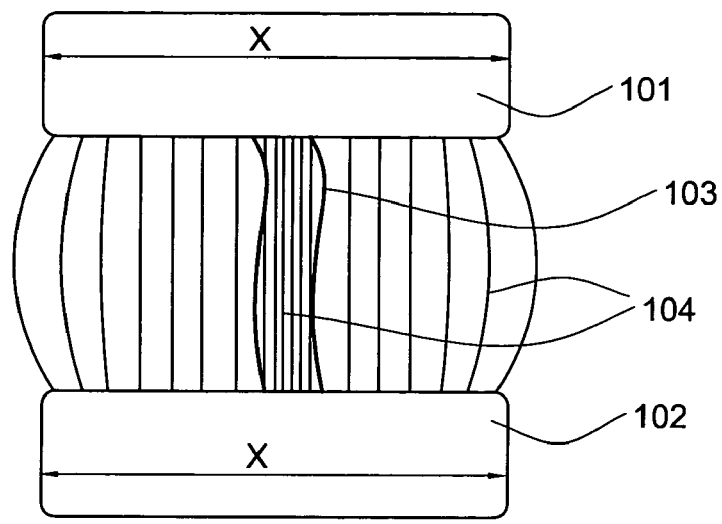
FIG. 2 shows the electrical current distribution in a skin region with blood vessel.

FIG. 2 shows schematically the electrical current distribution in a skin region including a blood vessel 103, when electrodes are applied to regions 101 and 102 of the skin. As shown in Table 1 above, blood has a three-fold higher electrical conductivity than wet skin. Thus, electrical current 104 through the blood vessel 103 is higher than in the surrounding skin, and hence the heating of blood vessel 103 is also higher than in the surrounding skin. At the periphery of edges of the contact regions 101 and 102, the electrical current is diverges, a phenomena known as "the boundary effect".

For the cosmetic removal of blood vessels, typically vessels at a depth of up to 2.5 mm are targeted. The distance between the electrodes should be larger than twice the depth of penetration (i.e. a separation of over 5 mm). The length of the contact regions 101 and 102 perpendicular to the blood vessel (the distance x in FIG. 2), should be much longer than the vessel diameter in order to avoid boundary effects near the vessel.

In order to coagulate a blood vessel it should be heated up to a temperature of at least 70° C. (T). The required heat power can be estimated as $$H = c\frac{\Delta T}{t}$$

where c is the blood heat conductivity (c~4.2 J/g° K.), t is the pulse duration and ΔT is the temperature increase. Pulse duration is estimated as the cooling time, for which a 0.5 mm diameter vessel is approximately equal to 100 msec. The current density through the vessel can be calculated as $$j = \sqrt{\frac{c\Delta T\sigma}{t}} \approx 3.2 \text{ A/cm}^2$$

with a contact length x of 1 cm (FIG. 2) and an RF current penetration depth of 0.25 cm, and taking into the account that the current density through the vessel is 3 times higher than the surrounding skin, the total current needed for the treatment is above 0.25A but not higher than 1A to avoid coagulation of the surrounding skin.

For the larger vessels, a longer pulse duration can be used.

Thus optimal range of parameters for the treatment of a vascular lesion is:

A bipolar electrode system is preferred but the use of a larger number of electrodes is possible.

The distance between electrodes is about twice the depth of the vessel (i.e. about 1 mm for the treatment superficial vessels to 2 cm for deeper vessels).

The length x (FIG. 2) should be larger than 3 mm in order to avoid boundary effects in the treated area.

The pulse duration depends on the vessel size and should be between 10 msec to 1000 ms.

The current density through the tissue should be in the range of 5 to 15 A/cm². This allows selective treatment of vascular lesions without damage to surrounding skin.

The electrodes should be positioned so as to create an electrical current parallel to the vessel.

Hair Removal

Figure 3:
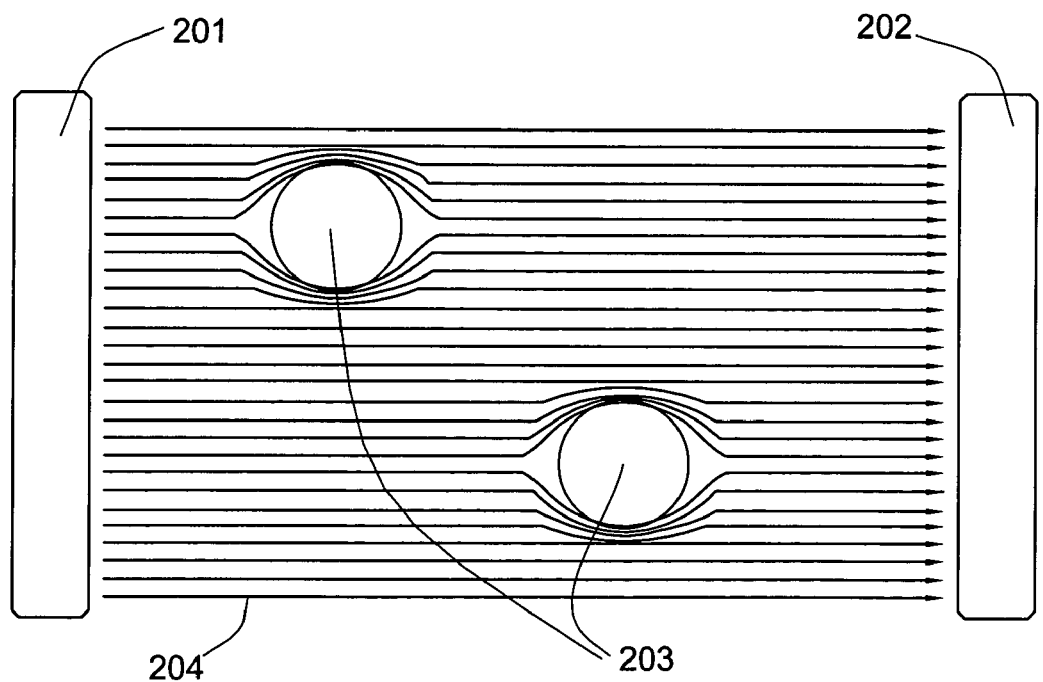
FIG. 3 shows the electrical current distribution around hair shaft.

FIG. 3 shows a skin region containing two hair shafts 203 shown in cross section. With hair removal, the main target is the hair follicle, which has the same electrical properties as the surrounding skin. However, the electrical conductivity of the shaft 203 is much lower than the conductivity of the skin. The hair shaft 203 does not conduct the electrical current 204, which must thus go around the shaft, thereby concentrating in a thin layer around the shaft as shown in FIG. 3. Detailed calculations show that the current density in the follicle can thus be twice that in the surrounding skin. According to Joule's law, the generated heat is proportional to the square of the current density. Thus, follicle heating is four times greater than the heating of the skin. The average current density through the skin needed to destroy the follicle can be calculated as $$j = \sqrt{\frac{\Delta T c\sigma}{4t}} \approx 1.9 \text{ A/cm}^2$$

The hair and follicle have an average diameter of about 250 microns and the optical pulse duration can be estimated to be 25 msec. Thus, the average current density applied to the skin should be higher than 1.9 A/cm² but lower than 8 A/cm².

The hair root depth varies for different locations and individuals from 1.5 mm to 4 mm. In order to be able to treat the entire range of hair depths the penetration depth of the RF current should be 4 mm and consequently, the distance between the electrodes should be as large as 8 mm.

The invention claimed is:

1. A method for non-invasive selective thermal destruction of a skin target by RF current comprising
    (a) determining one or more characteristics of an RF current and a bipolar RF electrodes system based upon one or more features of the target in order to create in the target an average energy density exceeding 5 Joules/cm³ but lower than a skin coagulation level; and
    (b) applying to the skin the determined electrode system and generating in the target an average energy density exceeding 5 Joules/cm³ but lower than a skin coagulation level.

2. The method according to claim 1 wherein the one or more characteristics of the RF current are selected from the group comprising (a) the RF current pulse duration, (b) the RF current frequency, (c) the distance between electrodes and (d) electrode shape.

3. The method according to claim 1 where the skin target is one of the group comprising a hair follicle, blood vessel, acne, and pigmented lesions.

4. The method according to claim 1 wherein the one or more features of the skin target are selected from the group comprising: (a) the type of target, (b) the depth of the target; and (d) the size of the target.

5. The method according to claim 1 wherein a characteristic of the RF current is the distance between the electrodes and a feature of the skin target is the depth of the skin target.

6. The method according to claim 5 wherein the distance between the electrodes is at least twice the depth of the skin target.

7. The method according to claim 1 wherein a characteristic of the RF current is the pulse duration and a feature of the skin target is the rate of cooling of the target.

8. The method according to claim 7 wherein the pulse duration is shorter than the cooling rate.

9. The method according to claim 1 wherein an average intensity of the RF energy in the skin is from about 5 to about 200 Joules/cm².

10. The method according to claim 1 wherein the electrodes have a circular contact area.

11. The method according to claim 1 further comprising cooling the electrodes.

* * * * *